United States Patent [19]

Scheefers et al.

[11] Patent Number: 5,622,837
[45] Date of Patent: Apr. 22, 1997

[54] PANCREAS ELASTASE 1-SPECIFIC ANTIBODY, A PROCESS FOR OBTAINING IT, AND A TEST KIT CONTAINING SUCH ANTIBODY

[75] Inventors: Hans Scheefers; Ursula Scheefers-Borchel, both of Wettenberg; Andreas Sziegoleit, Langgöns, all of Germany

[73] Assignee: ScheBo Tech Medizinisch-Biologische Forschungsgesellschaft mbH, Wettenberg, Germany

[21] Appl. No.: 457,172

[22] Filed: Jun. 1, 1995

Related U.S. Application Data

[63] Continuation of Ser. No. 220,395, Mar. 30, 1994, abandoned, which is a continuation of Ser. No. 969,173, filed as PCT/DE91/00606 Jul. 28, 1991 published as WO92/02630 Feb. 20, 1992, abandoned.

[30] Foreign Application Priority Data

Jul. 28, 1990 [DE] Germany ............ 40 23 972.1
Mar. 11, 1991 [DE] Germany ............ 41 07 765.2

[51] Int. Cl.$^6$ ................. C12N 5/00; C07K 16/40; G01N 33/53
[52] U.S. Cl. ............. 435/338; 530/388.1; 530/388.26; 530/389.1; 435/975
[58] Field of Search ............ 530/388.1, 388.26, 530/350, 389.1; 436/518, 531; 435/240.27, 975

[56] References Cited

FOREIGN PATENT DOCUMENTS 55-9120  1/1980  Japan.
63-73152  4/1988  Japan.

OTHER PUBLICATIONS

Wendorf et al. FEBS Lett., 1989, 249:275, Localization . . . elastapel.
Sziegoleit et al., Clin. Biochem., 1989, 22:85, Elastasel . . . Peces.
Macierer et al., Meth. Enzymol., 70:49, 1980, Proteins . . . Antigens.
Tani et al., J. Biol. Chem., 263:1231, 1988, Identification . . . Cloning.
Murata et al., Enzyme, 30:29, 1983, Radioimmunoassay . . . elastasel.
Sziegoleit et al., Biol Chem Hoppe Seyler, 368:1613, 1987.
Chem Abstracts, vol. 110 p. 284, 1989, Monoclonal . . . diagnosis, Kurata et al.
Chem. Abstracts, vol. 114, p. 97133, 1991, Enzyme . . . elastase, Hayakawa et al.

Primary Examiner—Frank C. Eisenschenk
Attorney, Agent, or Firm—John P. White

[57] ABSTRACT

A process is described for obtaining highly specific pancreas elastase 1 antibodies which react both with bodily fluids and with stools. Such an antibody is obtainable by immunizing with an antigen having the amino acid sequence Thr-Met-Val-Ala-Gly-Gly-Asp-Ile-Arg (SEQ ID NO:1) or immunologically active partial peptides thereof. A test kit containing such antibodies is suitable for the diagnosis and course monitoring of chronic and acute pancreatitis as well as mucoviscidosis in bodily fluids and/or in stools.

10 Claims, No Drawings

PANCREAS ELASTASE 1-SPECIFIC ANTIBODY, A PROCESS FOR OBTAINING IT, AND A TEST KIT CONTAINING SUCH ANTIBODY

This application is a continuation of U.S. Ser. No. 08/220,395, filed Mar. 30, 1994, now abandoned which is a continuation of U.S. Ser. No. 07/969,173, filed Mar. 29, 1993, now abandoned, corresponding to PCT International Application No. PCT/DE91/00606, filed Jul. 28, 1991, claiming priority of German Application Nos. P 41 07 765.2, filed Mar. 11, 1991 and P 40 23 972.1, filed Jul. 28, 1990.

This invention relates to a highly sensitive and selective anti-elastase 1 antibody, a process for its manufacture, and a highly sensitive diagnostic test kit containing said antibody.

Instances of inflammatory diseases of the pancreas are constantly increasing in industrial countries (W. Rösch, Deutsches Ärzteblatt 84: C-397–398, 1987). These diseases usually have an intermittent course and can finally lead to complete loss of the gland. Acute episodes are recognizable by severe abdominal pain and nausea, but intermediate phases are usually experienced by the patient as free from pain. They evolve only with uncharacteristic digestive complaints, so that they are hard to recognize. Consideration is therefore to be given to a chronic pancreatic disease in all digestive disorders.

Determination of the serum amylase level has hitherto usually been made in laboratory diagnoses of pancreatitis. However, an elevation in serum amylase also occurs in other intra-abdominal inflammations, e.g., in intestinal perforation, mumps or renal failure. Moreover, an elevation in the serum amylase level may also be observed following the administration of morphines. Another laboratory diagnostic possibility consists of determining the ratio of amylase to creatinine clearance, which ratio increases in acute pancreatitis. Unfortunately, amylase values elevated in acute pancreatitis normalize very rapidly, so that normal values are already found 48 hours after the onset of the disease in one-third of the patients (J. A. Eckfeldt et al., Arch. Pathol. Lab. Med. 109:316–319, 1985).

Lipase determination represents another diagnostic possibility. However, determination of either lipase or amylase is not suitable for detecting chronic pancreatitis. This disease has hitherto only been insufficiently demonstrated by determining the activity of the pancreatic enzyme chymotrypsin in stools. The disadvantage of this method of determination is based on the fact that only a small part of the chymotrypsin excreted by the pancreas is detectable in the stool, which part, moreover, is also subject to very considerable fluctuations (Goldberg et al., Gut 10:477–483, 1969). This makes the determination of normal values extremely difficult.

It is known from A. Sziegoleit, Biochem. J. 219:735–742, 1984, that pancreatic elastase 1 (E1), also called protease E, is exclusively formed in the pancreas and is separated out in the duodenum with digestive juice. Attempts have already been made to determine the level of elastase 1 in the stool to avoid the above-mentioned disadvantages, since the level of this enzyme in the stool represents the exocrine function of the pancreas substantially better than does the chymotrypsin activity (A. Sziegoleit et al., Clin. Biochem. 22:85–89, 1989).

It was also found that acute pancreatitis can be detected by determining E1 in serum (A. Sziegoleit et al., Clin. Biochem. 22:79–83, 1989).

It has hitherto been assumed that, unlike other enzymes, E1 is not degraded, or only unsubstantially degraded, during intestinal passage. Its level in the stool accordingly indicates the degree of pancreatic exocrine function. Moreover, the enzyme also enters the blood stream in acute pancreatic disease phases.

A radioimmunologic test is already available for measuring serum elastase 1 (A. Murata et al., Enzyme 30:29–37, 1983; Elastase-1-RIA-Kit, Abbott Diagnostic).

However, such a radiologic (RIA) determination presents a disadvantage, in that the radioactive reagents have only limited stability and therefore must continuously be resynthesized. Moreover, the radioactive material must be disposed of carefully, and the measurement of radioactive materials requires specially trained personnel and special laboratory equipment. In addition, it is not possible, or is only insufficiently possible, to determine the E1 level in the stool using this test.

The object of the invention is consequently that of developing a test process with which human elastase 1 can be determined for the diagnosis of both acute and chronic pancreatitis, and which is sufficiently sensitive for determining elastase 1 in serum and stools.

According to this invention, this object is achieved by means of an antibody directed against the epitope having the amino acid sequence Thr-Met-Val-Ala-Gly-Gly-Asp-Ile-Arg (SEQ ID NO:1). Surprisingly, it was found that antibodies directed against this epitope of human elastase 1 selectively recognize the marker enzyme and thereby discriminate against other antigens.

Accordingly, this invention also relates to a process for preparing anti-elastase antibodies in a known way, characterized by the fact that the previously defined epitope is used as an antigen. It is also possible, according to the invention, to use parts and fragments of this epitope for immunization or preparation of antibodies, provided the parts and fragments engender an immune response. Such fragments are obtainable either synthetically or by chemical and/or biological degradation of elastase 1. In the process of the invention, it was found suitable to bind the peptide or peptide part to a carrier, by means of a spacer if necessary. Suitable carriers are known to those skilled in the art and are, for example, synthetic and natural membrane parts, polysaccharides, peptides or proteins. Albumins and hemocyanins are especially preferable. The spacers to be used are also known to those skilled in the art. With the epitope or its fragments, it is possible, according to the invention, to obtain both selective monoclonal and polyclonal antibodies. Antibodies preferred according to the invention are able to recognize paraffin-embedded thin sections.

Antisera containing antibodies according to the invention are obtained by immunizing experimental animals with highly purified human elastase 1 or fragments of this enzyme. Experimental animals such as mice, rats, rabbits, goats or horses are thereby immunized in a known way, and antisera with polyclonal antibodies are thus obtained from which antibodies according to the invention are also obtainable in a known way. Antibodies preferred according to the invention are able to recognize paraffin-embedded thin sections.

In a preferred embodiment, monoclonal antibodies are suitably obtained by means of the epitope according to the invention using the method of G. Köhler and C. Milstein (Nature 256:495–497, 1975).

A further object of the invention is consequently a monoclonal antibody specifically capable of binding with E1. Such an antibody is obtainable by immunizing mice or rats with highly purified E1 or the epitope to be used according to the invention, fusing β-lymphocytes from the spleens of immunized animals with myeloma cells, cloning the hybridoma cells formed, cloning and culturing hybridoma cells which secrete antibodies capable of binding E1, and then obtaining the monoclonal antibodies formed by them.

It is especially preferable to use a cell line which does not itself produce any immunoglobulin.

The monoclonal antibodies obtainable according to the invention do not react with other substances, but are specific for E1. The monoclonal antibodies according to the invention are preferably able to recognize paraffin-embedded thin sections.

Antibodies preferred according to the invention are obtainable from hybridoma cell lines filed with the European Collection of Animal Cell Cultures (ECACC), Vaccine Research and Production Laboratory, Public Health and Laboratory Service, Center for Applied Microbiology and Research, Porton Down, Salisbury, Wiltshire SP4 OJG, Great Britain, on Dec. 19, 1990 in accordance with the requirements of the Budapest Treaty on the International Recognition of the Deposit of Microorganisms for the Purposes of Patent Procedure. The IC10A and IID54 hybridoma cell lines were given the Accession Numbers 90121906 and 90121907, respectively. Both antibodies obtainable from these cell lines are able to recognize paraffin-embedded thin sections.

Another object of the invention is the use of the E1-specific antibodies according to the invention for the qualitative and/or quantitative determination of E1. It is accordingly possible to specifically detect elastase 1 in bodily fluids and stools with the use of the antibody. The invention therefore also relates to a test kit containing antibodies according to the invention, especially immunologic test kits for the diagnosis and course monitoring of chronic pancreatitis, acute pancreatitis and mucoviscidosis in bodily fluids and/or stools. Suitable bodily fluids are blood, plasma and serum.

Indirect, competitive and sandwich ELISAs were introduced in experiments for detecting E1 in blood, plasma, serum or stools. However, it was found that a sandwich ELISA is most suitable for rapid diagnosis on a large specimen scale, since it is independent of other serum factors not capable of being calculated. At least two different monoclonal antibodies directed against different epitopes of the enzyme are necessary for this purpose.

Enzyme value changes in serum or stools, for example, can be demonstrated with such tests, especially the appearance of these displacements in the event of changes in pancreas status.

Determination processes based on the immunoassay principle have been widely developed. Advantages of these determination methods include precision and rapidity (great reliability and sample processing) as well as the possibility of being able to detect very small quantities of substance (in the nanogram range). Various process variants are possible for conducting the determination, with both homogeneous and heterogeneous phases. In the embodiment with the heterogeneous phase, one of the receptors is bound to a carrier. In the sandwich process, for example, a first antibody is bound to the carrier as a receptor, or a so-called catcher, and the test solution is added, whereby the antigen to be determined in the test solution is fished out and bound. A second tagged antibody is then added, which reacts specifically with the antigen or antigen-receptor complex. With the aid of a calibrated solution (isolated, purified human elastase 1), it is then possible to determine the quantity of antigen by tagging the second antibody.

In another preferred embodiment of the invention, a first antibody is bound as a receptor to a carrier matrix of membrane, tissue, or flowing structure, so that it does not represent the usual floor of the depression of an ELISA immunoplate, but is instead present as bound to the matrix. Preferred matrices are microporous flat membranes or hollow fiber membranes provided in a special embodiment with ion exchange groups. Microporous flat membranes such as those marketed by Pall Corp., New Jersey, USA, for example, are preferably used for this purpose. Hollow fiber membranes to be used according to the invention are also available on the market, and sold, for example, by Sepracor Inc. Massachusetts, USA. It is possible to develop particularly rapid and uncomplicated detection processes by means of such carrier materials.

Many variation possibilities exist for this general principle. For example, it is possible to make a determination with three receptors, whereby one of the three receptors is present in the heterogeneous phase, and the other two receptors are soluble. One of the two soluble receptors is tagged, whereas the other is untagged. The soluble receptor is then directed against the untagged receptor.

The use of the E1-specific antibody according to the invention for the selective quantitative determination of E1 based on the immunoassay principle is done by incubation with at least two different receptors. Both receptors, e.g., monoclonal antibodies, must be specific for E1, which must be bound to different epitopes (binding sites) in all cases.

One of the two receptors is bound to a solid phase. The binding to the solid phase is done in the usual way, as known to those skilled in the art. In addition, at least one other receptor is used, present in soluble form.

This other receptor bears a label. If several receptors are used, only one of them carries a label. Receptor tagging is done in a usual way, known to those skilled in the art.

Tagging in a test kit according to the invention is done in a known way, especially by radioactive tagging, binding of biotin (biotin/avidin), by an enzyme releasing a measurable reaction, or by a chemiluminescent or fluorescent compound. Tagging with an enzyme is especially preferred, particularly with peroxidase or phosphatase. In a special embodiment, tagging with an enzyme also permits the introduction of this antibody into a second enzyme amplification system (C. J. Stanley; F. Paris; A. Plumb; A. Webb; A Johansson, American Biotechnology Laboratory: May–June 1985; C. H. Self, J. Immunol. Meth. 1985).

In an especially preferred embodiment of this process, either a receptor capable of binding unspecifically to E1 or preferably a receptor capable of binding specifically to E1 is bound to a solid phase. This receptor bound to the solid phase is then incubated with the solution containing the E1 to be determined and an antibody which is specifically capable of binding with E1, present in soluble form, and bears a label.

If the receptor bound to the solid phase is capable of unspecifically binding with E1, not only E1 but other antigens also form a complex with the solid phase. The second antibody, which is capable of specifically binding to E1, nevertheless forms a complex only with E1, so that only E1 molecules specifically bear a tagged antibody, whereas other antigens are not labeled. After separation of the solid from the liquid phase, it is possible to determine the E1 content in this way by measuring the labeling.

If a first receptor capable of specifically binding to E1 is fixed to the solid phase, only E1 is specifically bound to the solid phase. During incubation with the soluble E1-specific second receptor or antibody, the latter also reacts exclusively with E1. Accordingly, since almost no binding of other antigens to the solid phase takes place, this process is highly specific and therefore makes very precise determinations possible. E1 is thereby selectively bound to the solid phase; other antigens remain in solution. In addition, the soluble labeled antibody capable of binding with E1 forms a complex with E1. After separation of the solid from the liquid phase, the E1 content can again be determined very precisely by the labeling. In a particularly preferred embodiment, a third antibody is added to further increase the selectivity. The third antibody is directed against the second antibody, which bears the label.

Other process variants with three receptors known to those skilled in the art are also possible using antibodies capable of specifically binding with E1. They do not require any further comments here.

Preferably at least one of the antibodies used for carrying out the process of the invention is a monoclonal antibody. In a preferred embodiment, only monoclonal antibodies are used as receptors.

The antibody specifically capable of binding to E1 can be present either bound to the solid phase or as a soluble tagged or untagged receptor. This receptor is preferably a monoclonal antibody. It is especially preferred for all receptors used to be monoclonal antibodies.

The process according to the invention, as well as the test kit, are especially suitable for automated analysis systems, especially for systems which are based on a biosensor and which make use of chip technology.

The invention is illustrated in greater detail by the following examples.

EXAMPLE 1 a) Preparation of Monoclonal Antibodies by Means of Highly Purified E1:

Highly purified human E1, the production of which from the human pancreas has been described (S. Sziegoleit, Purification and characterization of a cholesterol-binding protein from human pancreas. Biochem. J. 207:573–582, 1982), is dissolved in PBS and mixed in equal parts with Freund's adjuvant. In all cases, 100 µg of this mixture are injected IP and SC into Balb/c mice 6 to 8 weeks old. These injections are repeated twice at an interval of 3 to 4 weeks. In this design, mice immunized with highly purified E1 receive an IV injection of 100 µg of highly purified E1 dissolved in PBS 3 days before removal of the spleen.

About 100 million cells from the spleen of an immunized mouse are fused with 50 million myeloma cells (x 63-Sp8-653, a cell line which does not synthesize any immunoglobulin; obtainable from The Salk Institute, Cell Distribution Center, San Diego Calif. 92112, USA) in the presence of polyethyleneglycol (MG 3400). Fused cells are disseminated on 8 plates, each containing 24 depressions. Each of these depressions contains 50 million spleen cells, from unimmunized isologous mice, in nutrient medium containing hypoxanthine, aminopterin and thymidine.

The antibody-containing supernatant liquids of these fused cells (hybridomas) are tested 10 to 14 days later for their specificity to highly purified human E1 by means of ELISA, Western blot, frozen sections and paraffin sections.

To obtain monoclonal antibodies directed only against E1, hybridoma cells whose supernatant liquid does not contain any antibodies directed against other antigens are cloned two times.

b) Preparation of Monoclonal Antibodies by Means of an Immunogenic Peptide

The peptide having the amino acid sequence Thr-Met-Val-Ala-Gly-Gly-Asp-Ile-Arg is prepared by solid phase synthesis after Merrifield and, as described above, is injected into 6 to 8 week-old Balb/c mice. By the procedure described above, monoclonal antibodies which are highly specific against human elastase 1 from both stools and serum are obtained.

Determination of E1 in Plasma with Monoclonal E1-Specific Antibodies

EXAMPLE 2

E1 in plasma is determined by ELISA. For this purpose, monoclonal E1-specific antibodies obtained according to Example 1, which are dissolved in PBS at pH 7.2, are immobilized on polystyrene as a carrier. After a washing step, dilute E1-containing plasma or serum is added. The plasma or serum is diluted in a buffer of PBS, 5 mmol EDTA and 0.2% Tween 20.

After a washing step in PBS and 0.2% Tween 20, the E1 bound to the antibodies is incubated for one hour at room temperature with a polyclonal antibody which also binds E1 and is coupled to phosphatase, which is dissolved in PBS containing 0.2% Tween 20 at pH 7.2. After another washing step, p-nitrophenylphosphate disodium hexahydrate is added, and the change in optical density is measured in the reaction vessels in which the monoclonal antibodies have reacted with E1.

Determination of E1 in Plasma with Two Different E1-Specific Antibodies

EXAMPLE 3

A monoclonal antibody directed against E1 is fixed to a carrier as described in Example 2. After a washing step, E1-containing serum or plasma is incubated with the monoclonal antibodies under the same conditions as in Example 2. After another washing step, the binding of E1 is detected by a second E1-specific monoclonal antibody according to the invention. This second E1-specific antibody bears covalently bound peroxidase. After a washing step and addition of ABTS as a substrate for peroxidase, the change in optical density is measured.

EXAMPLE 4

The procedure is as described in Example 3, but biotin is coupled to the second E1-specific antibody instead of an enzyme. Peroxidase-conjugated avidin or peroxidase-conjugated streptavidin is added before the addition of substrate. The selected E1 determination thus made possible permits quite specific determination of only E1. Other antigens contained in the solution do not disturb the E1 determination according to the invention.

What is claimed is:

1. A process for obtaining monoclonal or polyclonal antibodies capable of specifically binding to human elastase 1 present both in bodily fluids and in stools, which comprises immunizing an experimental animal with an antigen having the amino acid sequence Thr-Met-Val-Ala-Gly-Gly-Asp-Ile-Arg (SEQ ID NO:1) or immunogenic partial peptides thereof conjugated to a carrier, and recovering resulting monoclonal or polyclonal antibodies capable of specifically binding to human elastase 1 present in human bodily fluids and in stools.

2. The process of claim 1, characterized in that the antigen is a synthetic partial peptide.

3. The process of claim 1, characterized in that the antigen is bound to a carrier by means of a spacer.

4. The process of claim 3, characterized in that a peptide is used as the carrier.

5. The process of claim 4, characterized in that an albumin or a hemocyanin is used as the carrier.

6. A hybridoma cell line having the file number ECACC 90 121 90 6.

7. A hybridoma cell line having the file number ECACC 90 121 90 7.

8. An anti-elastase 1 antibody obtained from hybridoma cell lines having the file number ECACC 90 121 90 6 or ECACC 90 121 90 7.

9. An immunological test kit for the diagnosis and course monitoring of chronic pancreatitis, acute pancreatitis, and mucoviscidosis in bodily fluids and/or stools which comprises the antibody of claim 8.

10. An immunological test kit for the diagnosis and course monitoring of chronic pancreatitis, acute pancreatitis, and mucoviscidosis in bodily fluids and/or stools which comprises the antibody of claim 8.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: protein ( v i ) ORIGINAL SOURCE:
        ( A ) ORGANISM: homo sapien
        ( G ) CELL TYPE: pancreatic ( x i ) SEQUENCE DESCRIPTION: SEQ ID NO:1:

Thr Met Val Ala Gly Gly Asp Ile Arg
    1                  5